United States Patent [19]

Doehner, Jr.

[11] Patent Number: 4,861,887

[45] Date of Patent: Aug. 29, 1989

[54] HERBICIDAL O-(SUBSTITUTED, AMINOMETHYLBENZOIC, NICOTINIC AND QUINOLINE-3-CARBOXYLIC ACIDS, ESTERS, AND SALTS

[75] Inventor: Robert F. Doehner, Jr., East Windsor, N.J.

[73] Assignee: American Cyanamid Company, Stamford, Conn.

[21] Appl. No.: 148,743

[22] Filed: Jan. 27, 1988

[51] Int. Cl.$^4$ .................. C07D 213/46; C07D 215/20
[52] U.S. Cl. ................................. 546/170; 546/318; 546/278; 560/37; 562/442; 71/92
[58] Field of Search .............. 546/170, 318; 560/37; 562/442

[56] References Cited

U.S. PATENT DOCUMENTS

| | | | |
|---|---|---|---|
| 4,188,487 | 2/1980 | Los | 548/301 |
| 4,297,128 | 10/1981 | Los | 548/302 |
| 4,638,068 | 1/1987 | Los | 546/169 |

*Primary Examiner*—Jane T. Fan
*Attorney, Agent, or Firm*—John W. Hogan, Jr.

[57] ABSTRACT

A method for the preparation of o-carboxyl imidazolinone compounds including oxidizing the appropriate 2-{[(1-carbamoyl-1,2-dimethylpropyl)amino]methyl}-benzoic acid intermediate with a brominating agent. Compounds useful as intermediates in the oxidation method and methods for preparing them are disclosed.

8 Claims, No Drawings

HERBICIDAL O-(SUBSTITUTED, AMINOMETHYLBENZOIC, NICOTINIC AND QUINOLINE-3-CARBOXYLIC ACIDS, ESTERS, AND SALTS

BACKGROUND OF THE INVENTION

This invention pertains to imidazolinone compounds and particularly to methods and intermediates useful for the preparation of o-carboxyarylimidazolinone compounds which are useful as herbicides.

Novel herbicidal imidazolinyl benzoic acids, nicotinic acids and quinoline-3-carboxylic acids, esters, and salts, and their preparation and use are disclosed in U.S. Pat. Nos. 4,188,487, 4,297,128, and 4,638,068.

SUMMARY OF THE INVENTION

The present invention provides a method for the preparation of o-carboxyarylimidazolinone compounds by oxidizing the appropriate 2-{[(1-carbamoyl-1,2-dimethylpropyl)amino]methyl}benzoic acid, nicotinic acid or quinoline-3-carboxylic acid with a brominating agent.

The invention also provides a method for preparing the intermediate 2-{[(1-carbamoyl-1,2-dimethylpropyl)amino]methyl} compounds by alkylating 2-methylvalineamides with the appropriate o-halomethylarylcarboxylate. In the case of pyridine halomethyl compounds, a 2-chloro-4-halo acetoacetate ester is reacted with an α,β-unsaturated aldehyde or ketone to form a 2-(halomethyl)nicotinic ester.

The invention further provides certain 2-{[(1-carbamoyl-1,2-dimethylpropyl)amino]methyl}benzoic acid, nicotinic acid, or quinoline-3-carboxylic acid compounds and certain 2-(halomethyl)benzoic esters, nicotinic esters, a quinoline-3-carboxylic ester compound useful as intermediates in the above methods.

The invention also provides a method for the preparation of o-carboxypyridyl imidazoline compounds by a sequence proceeding from the 2-chloro-4-haloacetoacetates, through reactions as described above, to oxidation of 2-{[(1-carbamoyl-1,2-dimethylpropyl)amino]-methyl} nicotinic acid ester with a brominating agent.

The oxidation method of this invention based on use of a bromine source provides unexpected results. Other oxidizing agents such as sulfur, chlorine, iodine and manganese oxide were ineffective for the result desired.

DESCRIPTION OF THE PREFERRED EMBODIMENTS o-Carboxyaryl imidazolinone compounds represented by formula I

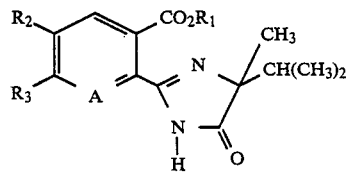

wherein
A is CH or N;
$R_1$ is H or $C_1$–$C_{12}$ alkyl;
$R_2$ is H or $C_1$–$C_6$ alkyl;
$R_3$ is H, $C_1$–$C_6$ alkyl, or when $R_2$ and $R_3$ are taken together they may form a ring represented by

are prepared by reacting a 2-{[(1-carbamoyl-1,2-dimethylpropyl)amino]methyl} nicotinic acid, or quinoline-3-carboxylic acid of formula II

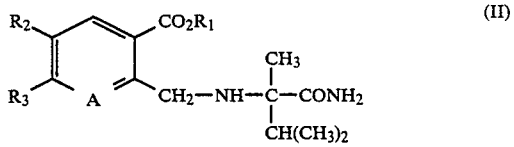

wherein A, $R_1$, $R_2$, and $R_3$ are as described for formula I above with a minimum of two molar equivalents of a brominating agent such as bromine, N-bromosuccinimide, N-bromoacetamide or the like in an inert organic solvent, such as acetic acid, in the presence of an acid acceptor such as sodium acetate, in a temperature range of about 20° C. to 100° C. for a sufficient period of time to essentially complete the reaction as illustrated in Flow Diagram I below.

FLOW DIAGRAM I

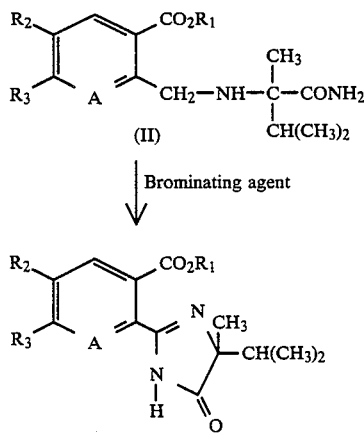

Formula II 2-{[(1-carbamoyl-1,2-dimethylpropyl)amino]-methyl} compounds suitable for use in the method of this invention may be prepared by reacting a 2-(halomethyl)-benzoic ester, nicotinic ester, or quinoline-3-carboxylic ester of formula III

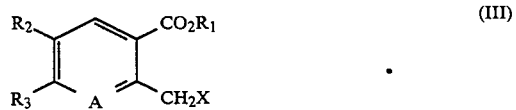

wherein $R_1$ is $C_1$–$C_{12}$ alkyl and A, $R_2$, and $R_3$ are as described for formula I above; and X is Cl or Br; with a minimum of one molar equivalent of racemic 2-amino-2,3-dimethylbutyramide or an individual optical isomer thereof, in an inert organic solvent such as dimethylsulfoxide, acetone or the like; in the presence of a base such as sodium bicarbonate; optionally in the presence of a catalytic amount of NaI; in a temperature range of about 25° C. to 100° C. as illustrated in flow diagram II below.

FLOW DIAGRAM II

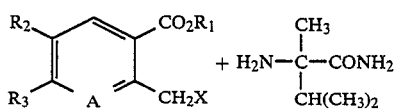

(III)

↓ Base, solvent

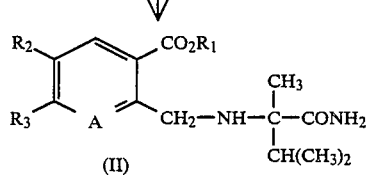

(II)

Formula II compounds wherein $R_1$ is hydrogen which are suitable for use in the method of this invention may readily be prepared from compounds of formula II wherein $R_1$ is $C_1$–$C_{12}$ alkyl by hydrolysis.

The present invention includes novel compounds represented by formula II below

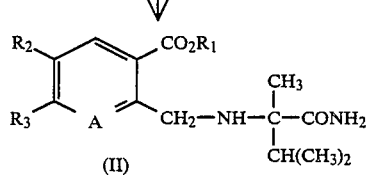
(II)

wherein
A is CH or N;
$R_1$ is H or $C_1$–$C_{12}$ alkyl;
$R_2$ is H or $C_1$–$C_6$ alkyl
$R_3$ is H, $C_1$–$C_6$ alkyl, or when $R_2$ and $R_3$ are taken together they may form a ring represented by —CH=CH—CH=CH—; and novel compounds by formula III below

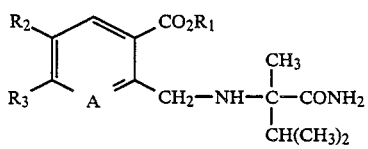
(III)

wherein $R_1$=$C_1$–$C_{12}$ alkyl and $R_2$ and $R_3$ are described for formula II above, and X is Cl or Br, which are useful intermediates for the preparation of herbicidal imidazolinone compounds utilizing the methods of this invention. A preferred group of novel formula II and formula III compounds above are those wherein
$R_1$ is $C_1$–$C_3$ alkyl;
$R_2$ is H, or $C_1$–$C_3$ alkyl; and
$R_3$ is H.

Formula III pyridine halomethyl compounds for use in the method of this invenion may be prepared by a method analogous to that described in pending application for U.S. Letters Patent of R. Doehner, Ser. No. 791,671 filed Oct. 28, 1985 by reacting a 2-chloro-4-haloacetoacetate ester of formula IV

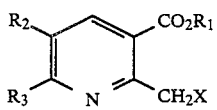
(IV)

wherein $R_1$ is $C_1$–$C_{12}$ alkyl; and X is Cl or Br with an α,β-unsaturated aldehyde or ketone of formula V

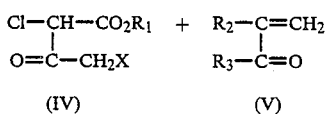
(V)

wherein $R_2$ is H or $C_1$–$C_6$ alkyl and $R_3$ is H in the presence of a minimum of two molar equivalents of ammonium salt in an organic solvent, in a temperature range of ambient temperature to the boiling point of the solvent until the reaction is essentially complete, as illustrated in Flow Diagram III below.

FLOW DIAGRAM III

(IV)     (V)

↓ solvent
ammonium salt
≧2 molar equivalents

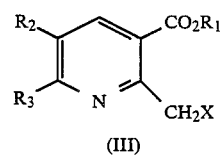

(III)

wherein $R_1$, $R_2$, $R_3$ and X are as described for formula IV and Formula V above.

The present invention also includes a method for the preparation of o-carboxypyridyl imidazolinone compounds represented by formula I

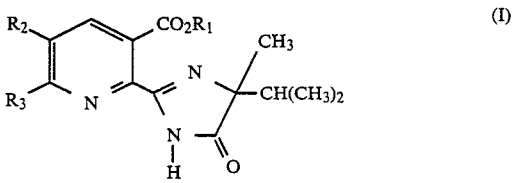
(I)

wherein
$R_1$ is H, or $C_1$–$C_{12}$ alkyl;
$R_2$ is H, or $C_1$–$C_6$ alkyl; and
$R_3$ is H;
by reacting, in sequence, a 2-chloro-4-haloacetoacetate ester of formula IV

(IV)

with an α,β-unsaturated aldehyde or ketone of formula V

(V)

in the presence of a minimum of two molar equivalents of ammonium salt in an organic solvent, in a temperature range of ambient temperature to the boiling point of the solvent until the reaction is essentially complete, and reacting the thus formed 2-(halomethyl)nicotinic ester, of formula III

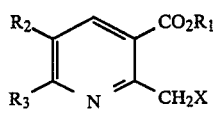

wherein $R_1$, $R_2$, $R_3$ and X are as previously described for formula IV and V, with a minimum of one molar equivalent of racemic 2-amino-2,3-dimethylbutyramide or an individual optical isomer thereof in an inert organic solvent in the presence of a base, optionally in the presence of a catalytic amount of NaI, in a temperature range of about 25° C. to 100° C., and further reacting the thus-formed 2-{[(1-carbamoyl-1,2-dimethylpropyl)amino]methyl}nicotinic ester, or acid derived therefrom, of formula II

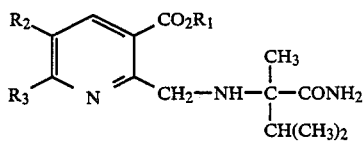

wherein $R_1$, $R_2$ and $R_3$, are as described for formula I above with a minimum of two molar equivalents of a brominating agent in an inert organic solvent in the presence of an acid acceptor in a temperature range of about 25° C. to 100° C. for a sufficient period of time to essentially complete the reaction.

The preparation of other intermediates of formula III closely follows literature procedures such as oxidation of a 2-methyl-3-pyridinecarboxylate or a 2-methyl-3-quinolinecarboxylate, followed by rearrangement of the resulting N-oxide with $POCl_3$, to give compounds of formula III as illustrated below.

is heated at reflux for 90 minutes. The reaction is concentrated in vacuo and the residue is partitioned between ethyl acetate and water. The organic phase is concentrated in vacuo, and the residue is chromatographed on silica gel using hexane-ethyl acetate mixtures to give 50 g of crude product. This material is purified by extraction into aqueous hydrochloric acid, washing with hexanes, making the aqueous phase basic with cold ammonium hydroxide, and extracting with hexanes to afford 30 g of the title product as an oil (43%), having elemental analysis calculated for $C_{11}H_{14}ClNO_2$ %C 58.03, H 6.20, N 6.15, Cl 15.57 found %C 58.29, H 6.30, N 6.02, Cl 15.49.

Utilizing the above procedure yields the formula III compounds listed in Table I below.

TABLE I

| | | | | | | (III) |
|---|---|---|---|---|---|---|
| mp | $R_1$ | $R_2$ | $R_3$ | X | analysis (calc) | |
| low-melting solid | $C_2H_5$ | $CH_3$ | H | Cl | C, 56.13 (56.22) H, 5.65 (5.66) N, 6.57 (6.56) Cl, 16.40 (16.59) | |
| oil | $CH_3$ | $C_2H_5$ | H | Cl | C, 55.68 (56.22) H, 5.63 (5.66) N, 6.25 (6.56) Cl, 16.70 (16.59) | |
| low-melting | $CH_3$ | $CH_3$ | H | Cl | C, 54.12 (54.15) H, 5.07 (5.05) N, 6.98 (7.02) Cl, 17.79 (17.76) | |
| low-melting | $C_2H_5$ | $CH_3$ | H | Br | C, 47.86 (46.53) H, 4.75 (4.69) N, 5.51 (5.43) Br, 31.28 (30.96) | |

EXAMPLE 2

Preparation of ethyl 2-chloromethylnicotinate

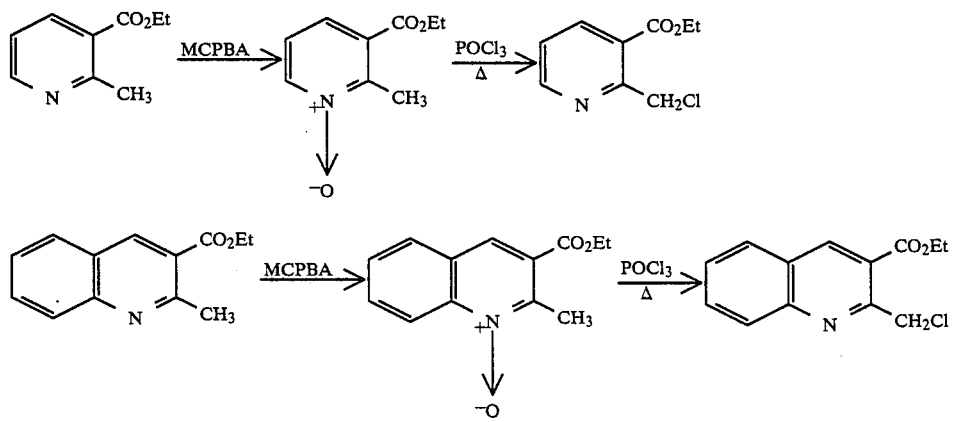

The invention is further illustrated by the following non-limiting examples.

EXAMPLE 1

Preparation of ethyl 2-chloromethyl-5-ethylnicotinate

A solution of 61 g of ethyl-2,4-dichloroacetoacetate (0.306 mol) and 30 g of 2-ethylacrolein (0.357 mol) in 500 mL of absolute ethanol is mixed with 85.5 g of ammonium sulfamate (0.75 mol), and the stirred mixture A solution of 9 g of ethyl 2-methylnicotinate in 250 mL methylene chloride is stirred at room temperature and 32 g of 80% metachloroperoxybenzoic acid is added in one portion. The resulting solution is stirred for three days. The precipitated solid is filtered off, and the filtrate is washed with cold, dilute aqueous sodium hydroxide, dried, and concentrated in vacuo to afford the crude N-oxide. This material is digested in 75 mL of 1,2-dichloroethane; 15 mL of phosphorous oxychloride is added, and the solution is heated at reflux overnight. The solution is concentrated in vacuo, and the residue is taken up in methylene chloride and neutralized with aqueous sodium acetate. The organic phase is dried, concentrated in vacuo, and the residue is chromatographed on silica gel using hexane-ethyl acetate mixtures to afford 1.2 g of the title product as an oil having NMRδmCDCl(3): 1.4 (+, 3H), 4.5 (q, 2H), 5.1 (2H), 7.4 (1,H), 8.4 (dd, 1H), 8.8 (dd, 1H).

Also prepared by this method is ethyl 2-chloromethylquinoline-3-carboxylate; NMR(δCDCl₃) 1.4 (+, 3H), 4.5 (q, 2H), 5.3 (5,2H), 7.5-8.3 (m, 4H), 9.0 (5, 1H).

EXAMPLE 3

Preparation of ethyl 2-{[(1-carbamoyl-1,2-dimethylpropyl)amino]methyl}-5-ethylnicotinate A mixture of 77 g of ethyl 2-chloromethyl-5-ethylnicotinate (0.338 mol), 44 g of o-methylvalinamide (0.338 mol) and 33.5 g of sodium bicarbonate (0.4 mol) in 60 mL dimethylsulfoxide is stirred and heated at 80° for 16 hours. The reaction is partitioned between 1:1 ethylacetate-hexane and water. The organic layer is washed thoroughly with water, dried, and concentrated in vacuo to a gum. Chromatography of this gum on silica gel using hexane-ethyl acetate mixtures as eluant affords the title product, mp 68-72°.

The above reaction is conducted with acetone as solvent (with cat. NaI) and also yields the title product.

Utilizing the above procedure with analogous formula III halomethyl compounds yields the formula II compounds listed in Table II below.

TABLE II (II) structure: $R_2$, $R_3$, A, ring with $CO_2R_1$ and $CH_2NH-C(CH_3)(CH(CH_3)_2)-CONH_2$

| mp °C. | R₁ | R₂ | R₃ | A |
|---|---|---|---|---|
| 106-107 | CH₃ | CH₃ | H | N |
| solid | C₂H₅ | H | H | N |
| 138-139 | C₂H₅ | —CH=CH—CH=CH— | | N |
| 81-83 | C₂H₅ | H | H | CH |

EXAMPLE 4

Preparation of ethyl 5-ethyl-2-(4-isopropyl-4-methyl-5-oxo-2-imidazolin-2-yl)nicotinate A mixture of 1 g of ethyl 2-{[(1-carbamoyl-1,2-dimethylpropyl)amino]methyl}-5-ethylnicotinate (3.1 mmol) and 0.58 g anhydrous sodium acetate (7 mmol) in 10 mL acetic acid is warmed to 50° C., at which point the reaction is a homogeneous solution. A solution 1 g of bromine (6.2 mmol) in 2 mL acetic acid is added in two portions over two minutes, and the reaction is stirred at 50° C. for 16 hours. The reaction mixture is concentrated in vacuo, and the residue is partitioned between ethyl acetate and water. The organic layer is washed with aqueous sodium bisulfite, dried over MgSO₄, diluted with an equal volume of hexanes, and filter-chromatographed through a pad of silica gel. The silica gel is further eluted with additional 1:1 hexane-ethyl acetate, and the combined eluates are concentrated in vacuo to afford 0.6 g product having mp 84.5°-86.5° C.

The title product is also obtained using N-bromoacetamide or N-bromosuccinimide in place of bromine.

Utilizing the above procedure with various formula II compounds yields the formula I compounds listed in Table III below.

TABLE III (I) structure: $R_2$, $R_3$, A, ring with $CO_2R_1$ and imidazolinone substituent containing $CH_3$, $CH(CH_3)_2$, N-H, C=O

| R₁ | R₂ | R₃ | A | mp °C. |
|---|---|---|---|---|
| CH₃ | CH₃ | H | N | 129.0-130.5 |
| C₂H₅ | H | H | N | 72.0-75.0 |
| C₂H₅ | —CH=CH—CH=CH— | | N | 146.0-147.5 |
| H | H | H | CH | 163.0-165.0 |

EXAMPLE 5

Preparation of 2-{[(1-carbamoyl-1,2-dimethylpropyl)amino]methyl}-5-ethylnicotinic acid A solution of 5.6 g of ethyl 2-{[(1-carbamoyl-1,2-dimethylpropyl)amino]methyl}-5-ethylnicotinate (0.0174 mol) in 30 mL of methanol containing 2 g of NaOH (0.05 mol) and 10 mL water is stirred at room temperature for two hours and 30 minutes. The reaction is concentrated in vacuo and redissolved in 30 mL water; adjustment of the pH to 4 with concentrated hydrochloric acid and concentration in vacuo gives a gum. This residue is dissolved in a mixture of ethyl acetate, tetrahydrofuran, and methanol, dried over MgSO₄, and concentrated in vacuo to 6 g foam. Crystallization from methanol-ether affords 3.1 g product, mp 180°-181° C.

EXAMPLE 6

Preparation of 5-ethyl-2-(4-isopropyl-4-methyl-5-oxo-2-imidazolin-2-yl)nicotinic acid A mixture of 0.8 g of 2-{[(1-carbamoyl-1,2-dimethylpropyl)amino]methyl}-5-ethylnicotinic acid (2.7 mmol) and 0.56 g sodium acerate (6.8 mmol) in 10 mL acetic acid is warmed until homogeneous and cooled to room temperature. The solution is treated with 0.88 g bromine (5.45 mmol), and the reaction is stirred at 25° C. for 16 hours, then at 75° C. for three days. The reaction mixture is partitioned between CH₂Cl₂ and water, and the organic phase is dried and concentrated in vacuo. The residue is recrystallized from ethyl acetate-hexanes to afford 0.4 g of the title product having mp 172°-175° C.

What is claimed is:

1. A 2-{[(1-carbamoyl-1,2-dimethylpropyl)-amino]methyl}benzoic acid, nicotinic acid or quinoline-3-carboxylic acid compound represented by formula II

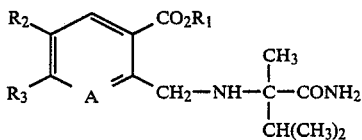
(II)

wherein
A is CH, or N;
$R_1$ is H or $C_1$–$C_{12}$ alkyl;
$R_2$ is H or $C_1$–$C_6$ alkyl;
$R_3$ is H, $C_1$–$C_6$ alkyl, or when $R_2$ and $R_3$ are taken together they may form a ring represented by

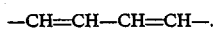

2. A compound according to claim 1 wherein
$R_1$ is H or $C_1$–$C_3$ alkyl;
$R_2$ is H or $C_1$–$C_3$ alkyl; and
$R_3$ is H.

3. The compound according to claim 1 wherein the compound is ethyl 2-{[(1-carbamoyl-1,2-dimethylpropyl)amino]methyl}benzoate.

4. The compound according to claim 1 wherein the compound is ethyl 2-{[(1-carbamoyl-1,2-dimethylpropyl)amino]methyl}-5-ethylnicotinate.

5. The compound according to claim 1 wherein the compound is methyl 2-{[(1-carbamoyl-1,2-dimethylpropyl)amino]methyl}-5-methylnicotinate.

6. The compound according to claim 1 wherein the compound is ethyl 2-{[(1-carbamoyl-1,2-dimethylpropyl)amino]methyl}nicotinate.

7. The compound according to claim 1 wherein the compound is ethyl 2-{[(1-carbamoyl-1,2-dimethylpropyl)amino]methyl}-3-quinolinecarboxylate.

8. The compound according to claim 1 wherein the compound is 2-{[(1-carbamoyl-1,2-dimethypropyl)amino]methyl}-5-ethylnicotinic acid.

* * * * *